United States Patent [19]
Winterer et al.

[11] Patent Number: 5,810,323
[45] Date of Patent: Sep. 22, 1998

[54] PINCH CLIP OCCLUDER FOR INFUSION SETS

[75] Inventors: Sean Winterer, Midvale; Chris Dumas, Sandy; Michael Child, Kearns; David J. McNally, Sandy, all of Utah

[73] Assignee: Zevex, Inc., Salt Lake City, Utah

[21] Appl. No.: 712,577

[22] Filed: Sep. 13, 1996

Related U.S. Application Data

[63] Continuation of Ser. No. 410,912, Mar. 27, 1995, abandoned.

[51] Int. Cl.⁶ ........................................... F16K 7/04
[52] U.S. Cl. .......................................... 251/4; 251/7
[58] Field of Search .......................... 251/7, 4, 9

[56] References Cited

U.S. PATENT DOCUMENTS

| | | |
|---|---|---|
| 3,329,391 | 7/1967 | Deane . |
| 3,998,364 | 12/1976 | Hollander ................................. 251/7 X |
| 4,382,453 | 5/1983 | Bujan et al. . |
| 4,453,295 | 6/1984 | Laszczower . |
| 4,524,802 | 6/1985 | Lawrence et al. . |
| 4,559,045 | 12/1985 | Danby et al. . |
| 4,624,663 | 11/1986 | Danby et al. . |
| 4,634,092 | 1/1987 | Daniell et al. ............................... 251/7 |
| 4,728,324 | 3/1988 | Steigerwald et al. .................. 251/7 X |
| 4,960,259 | 10/1990 | Sunnanvader et al. . |
| 5,238,218 | 8/1993 | Mackal . |

Primary Examiner—John Fox
Attorney, Agent, or Firm—Thorpe, North & Western, LLP

[57] ABSTRACT

A pinch clip occluder for infusion sets is disclosed including a housing and a clamp movably disposed within the housing to selectively occlude an infusion set. In one embodiment the clamp has at least one arm which moves between first and second positions to pinch closed a silicone tube of the infusion set unless the pinch clip occluder is held in an open position by the user, or placed in a receptacle which will hold the pinch clip occluder in an open position. In another embodiment a plunger is disposed so as to intersect a passage passing through the housing. As the plunger is selectively moved between first and second positions, the flow through a tube in the passage is selectively controlled. Such an arrangement prevents a free-flow condition from occurring through the infusion set.

15 Claims, 7 Drawing Sheets

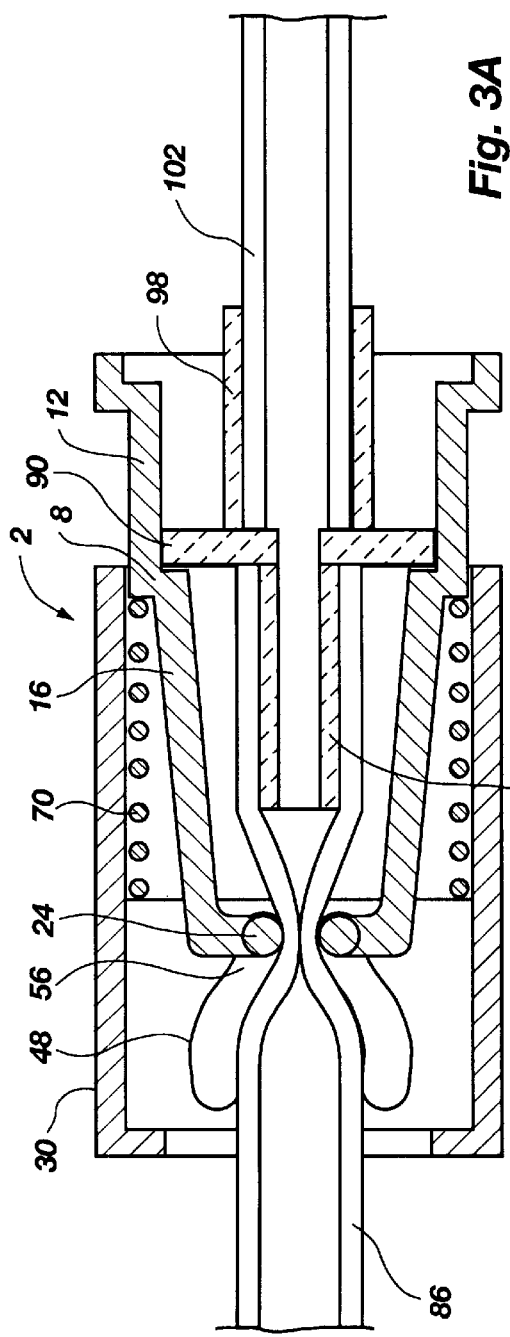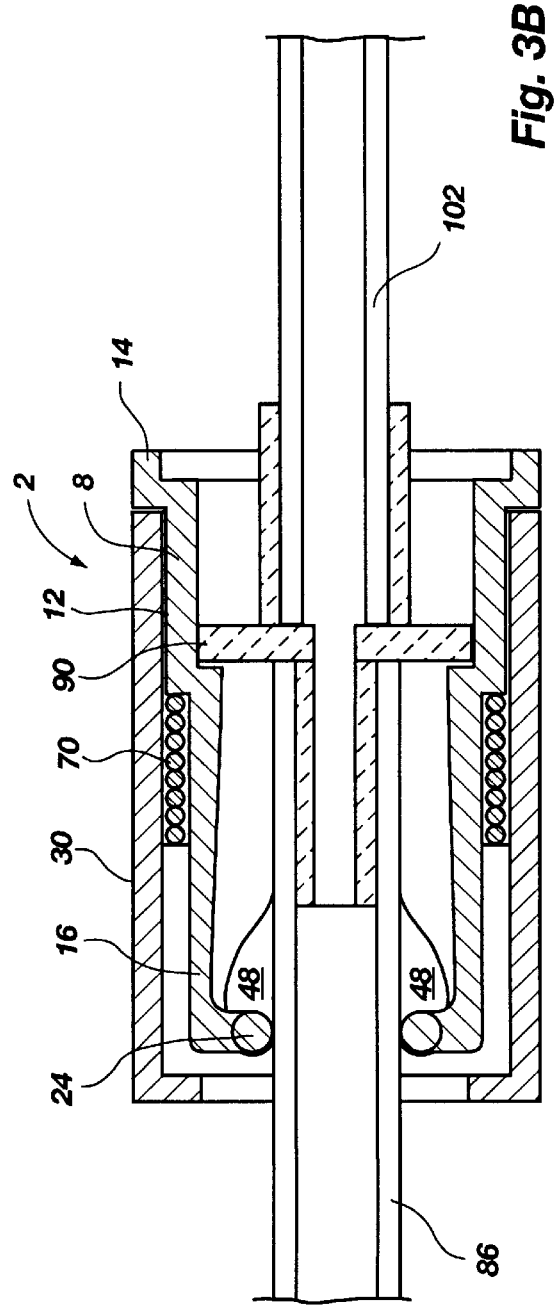

5,810,323

PINCH CLIP OCCLUDER FOR INFUSION SETS

This application is a continuation of U.S. application Ser. No. 08/410,912, filed Mar. 27, 1995, of Winterer, et al. for PINCH CLIP OCCLUDER FOR INFUSION SETS, now abandoned.

BACKGROUND OF THE INVENTION

The present invention relates to an occluder device for the administration of enteral and/or parenteral solutions, and in particular to a pinch clip occluder for infusion sets.

The use of infusion sets to administer solutions to patients is well known in the medical arts. Infusion sets are used for both enteral and parenteral applications. Enteral feeding pumps are used to provide patients with nutrition and medication when they are unable, for a variety of reasons, to eat normally. Parenteral (intravenous) solutions are provided to patients to ensure adequate hydration and to provide needed nutrients, minerals and medication. Often, the infusion set is placed in a free standing arrangement in which gravity forces the solution into the patient. The rate at which the solution enters the patient can be roughly controlled by various clamps, such as roller clamps, which are currently available on the market.

In many applications, it is necessary to precisely control the amount of solution which enters the patient. When this is the case, a regulating device, such as an enteral feeding pump, is placed along the infusion set to control the rate at which the solution is fed to the patient. In applications where a pump, etc., is used, the clamps used to regulate flow are typically manually opened, when employed, as they may interfere with the proper functioning of the pump. When used, the roller clamp may be closed to stop flow through the infusion set with the intention that the medical personnel will momentarily connect the pump or other regulating device to the infusion set. However, emergencies or other distractions may prevent the medical personnel from properly attaching the pump or other regulating device or properly operating the clamp.

When the infusion set is not properly positioned in the pump, etc., a situation known as free-flow often develops. The force of gravity causes the solution to flow freely into the patient unchecked by the pump or other regulating device. Under a free-flow condition, an amount of solution many times the desired dose can be supplied to the patient within a relatively short time period. This can be particularly dangerous if the solution contains potent medicines and the patient's body is not physically strong enough to adjust to the large inflow of solution.

Thus, there is a need for a device that prevents a free-flow condition if the infusion set is not properly mounted in the pump or other regulating means.

SUMMARY OF THE INVENTION

It is an object of the present invention to provide a safety occluder for infusion sets which prevents an accidental free-flow condition.

It is another object of the present invention to provide an occluder which is simple to make and use.

It is another object of the present invention to provide such an occluder which is inexpensive and thus disposable.

The above and other objects of the invention are realized in a pinch clip occluder biased in an occluding position to prevent free-flow conditions. In one embodiment of a pinch clip, the occluder includes a housing with a passage therethrough and a pinch clamp nestable in the housing. The pinch clamp includes arms which are typically biased in a closed position when no external force is acting thereon, but may be moved into an open/nonoccluding position by movement of the clamp relative to the housing.

In another illustrated embodiment, the occluder includes a housing with a passage therethrough for receiving a delivery set. A plunger disposed along the housing is movable between two positions, one of which occludes flow through the delivery set and the other of which allows flow through the delivery set. To overcome the risk of a free-flow condition, the plunger is typically biased in an occluding position.

In accordance with one aspect of the invention, a biasing member, such as a spring, is disposed between the housing and part of the plunger or pinch clamp to bias the plunger or pinch clamp in a closed position until the infusion set is properly mounted in a flow regulating device, such as an enteral feeding pump.

BRIEF DESCRIPTION OF THE DRAWINGS

The above and other objects, features and advantages of the invention will become apparent from a consideration of the following detailed description presented in connection with the accompanying drawings in which:

FIG. 3A shows a side cross-sectional view of a pinch clip occluder made in accordance with the principles of the present invention, and disposed in an occluding mode;

FIG. 3B shows a side cross-sectional view of a pinch clip occluder made in accordance with the principles of the present invention, and disposed in a nonoccluding mode;

DETAILED DESCRIPTION

Figure 1:
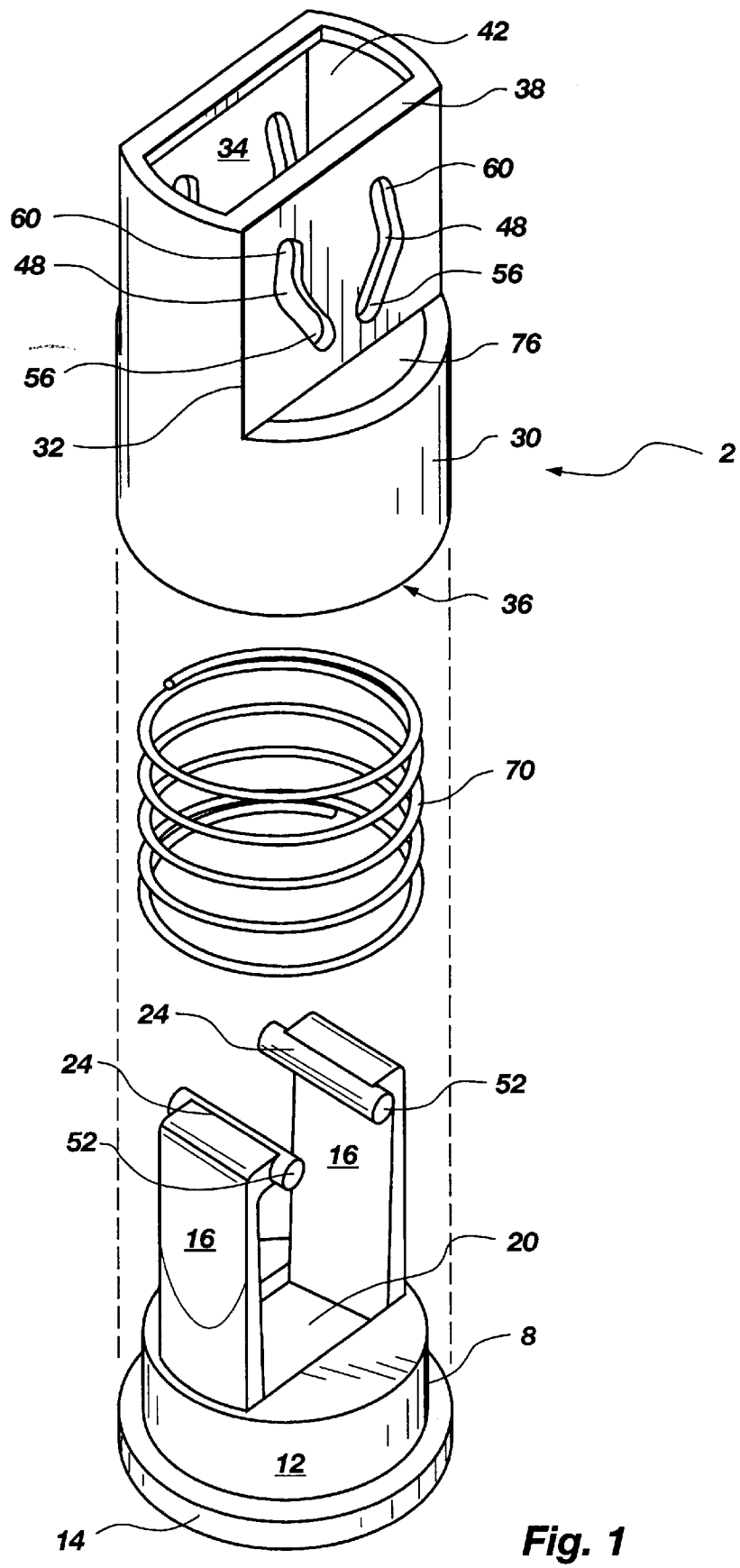
FIG. 1 shows a perspective/exploded view of the pinch clip occluder made in accordance with the principles of the present invention.

Reference will now be made to the drawings in which the various elements of the present invention will be given numeral designations and in which the invention will be discussed so as to enable one skilled in the art to make and use the invention. Referring to FIG. 1, there is shown an exploded view of a pinch clip occluder for infusion sets, generally indicated at 2. The pinch clip 2 includes a clamp 8 having a base 12 with a flange 14 around the bottom of the base. A pair of pincher arms 16 extend from the base 12 opposite the flange 14. A passage 20 in the base 12 enables a tube of an infusion set, not shown, to pass through the base, and between the arms 16. The arms 16 are biased in a closed position so that a pair of heads 24 (one on each arm) are sufficiently close together to occlude a tube of an infusion set passing between the heads, i.e. pinching sides of the tube of the infusion set together between the heads so that solution cannot flow through that portion of the tube.

The pinch clip 2 also includes an adjustment means in the form of a housing 30 formed by a generally cylindrical wall 32. The housing 30 is designed so that the clamp 8 will fit inside a hollow 34 extending through the housing. The hollow 34 begins at an open first end 36 of the housing 30 and terminates at an open second end 38 of the housing 30 in a passage 42. When the clamp 8 is nested in the housing 30, the passage 42 in the second end 38 of the housing is in axial alignment with the passage 20 in the clamp. The axial alignment of the two passages 20 and 42 allows the tubing of an infusion set, not shown, to be passed through the pinch clip 2.

The housing 30 has a pair of channels 48 formed in at least one position along the wall 32. The channels 48 are designed to receive projections 52 extending outwardly from each head 24 on the arms 16. The channels 48 are sloped so that lower ends 56 of the channels are separated from each other by about the same distance as the heads 24 of the arms 16 when in the biased, closed position. Thus, when the projections 52 are disposed at the lower end 56 of the channels 48, the arms 16 remain in their biased state and preclude fluid from passing through an infusion set passing therethrough.

The upper ends 60 of the channels 48 are disposed further apart than the lower ends 56. Thus, if the clamp 8 is pushed upwardly into the housing 30 so that the projections 52 move from the lower ends 56 of the channels 48 to the upper ends 60, the projections 52, the heads 24 and thus the arms 16 are forced apart, overcoming the biasing of the arms. When the projections 52 are disposed at the upper end 60 of the channels 48, the heads 24 of the clamp 8 are held apart sufficiently that fluid can flow freely through the infusion set.

Also shown in FIG. 1 is a spring 70. The spring 70 is positioned adjacent the base 12 of the clamp 8 so that the bottom of the spring rests on the base. When the clamp 8 is nested in the housing 30, the top of the spring 70 rests against a lip 76 below the channels 48. The natural bias of the spring 70 is to push the clamp 8 out of the housing 30. The clamp 8, however, cannot be totally pushed out of the housing 30, because the projections 52 catch at the lower ends 56 of the channels 48. Thus, the spring 70 biases the clamp 8 into a position in which the heads 24 on the arms 16 will occlude an infusion set passing therethrough. When the clamp 8 is pushed into the housing 30, overcoming the force of the spring 70, the arms 16 will spread further apart as the projections 52 follow the channels 48 to the upper ends 60.

Figure 2:
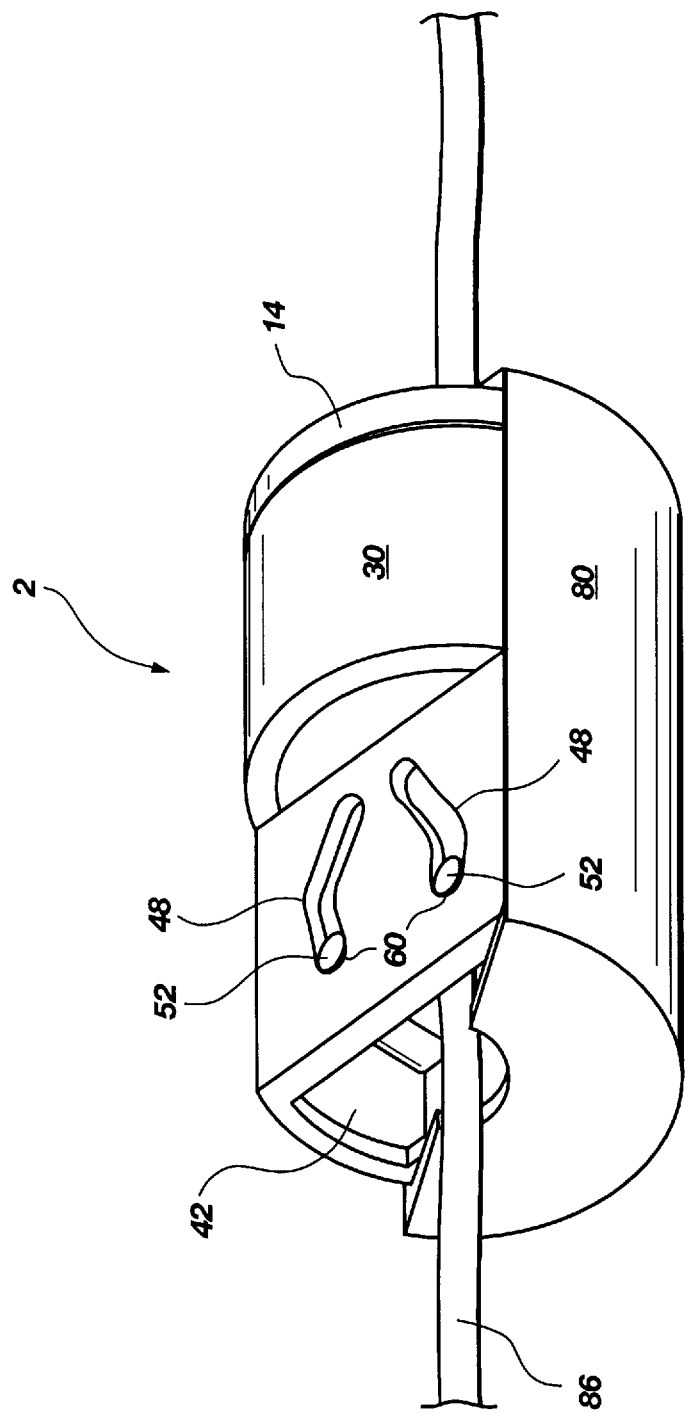
FIG. 2 shows a perspective view of the pinch clip of FIG. 1 mounted in a receptacle for maintaining the pinch clip in an open position, and a fragmented view of an infusion set passing through the pinch clip.

Referring now to FIG. 2, there is shown a perspective view of the pinch clip 2 disposed in a receptacle 80 formed as a half cylinder. In order to place the pinch clip 2 into the receptacle 80, the clamp (disposed within the housing) must be pushed into the housing 30 sufficient for the bottom of the housing to touch the flange 14, or be positioned very close thereto. When the clamp is in such a position, the projections 52 are forced to the upper ends 60 of the channels 48 so that the heads (not shown) do not occlude the infusion set 86. Such a receptacle 80 will typically be formed in devices such as enteral feeding pumps (not shown) which receive an infusion set, rather than being formed separately. No solution can flow through the infusion set 86 unless the pinch clip 2 is properly placed in the receptacle 80. Thus, medical personnel cannot accidently create a free-flow state by forgetting to thread the infusion set 86 through an enteral feeding pump, because the pinch clip 2 will occlude flow unless properly mounted in the receptacle of the feeding pump. If the infusion set is accidentally pulled out of the pump, the pinch clip 2 will automatically spring into an occluding position, thereby preventing free-flow of the solution.

Those skilled in the art will recognize that each component of the pinch clip 2 and the receptacle 80 could be made of numerous different materials. However, it is anticipated that the all of the structures, except the spring 70 (FIG. 1) will be made of polyvinylchloride (PVC), or polycarbonate materials which are inexpensive and easy to fabricate into the structures described. Such materials would also make the pinch clips 2 disposable. If greater durability is desired, materials such as advanced engineering plastics or metal can also be used.

Referring now to FIG. 3A, there is shown a cross-sectional view of the pinch clip 2 in an occluding (closed) mode in that the heads 24 of the arms 16 are in a first position in the lower ends 56 of the channels 48 in the housing 30. The heads 24 are close enough together so that they pinch the sidewall of the tubing 86 together and prevent fluid flow therethrough. The clamp 8 is held in this position by the spring 70 which is fully extended.

Also shown in FIG. 3A is an adapter 90 which has a first connector 94 for fitting within the tubing 86, and a second connector 98 to fit around the tubing 102. The adapter 90 nests within the base 12 of the clamp 8.

Typically, an infusion set, such as that used with enteral feeding pumps, will have a pair of long sections of tubing formed from a material such as PVC, and an interspaced section of tubing made of silicone. In the present discussion, the tubing 86 represents the silicone tubing and the tubing 102 typically represents the proximal PVC tubing positioned upstream from an enteral feeding pump. The silicone tubing 86 is used to pass through an enteral feeding pump because it withstands the flexing and pulling of the pump rotor better than does the PVC tubing 102. An adapter, such as adapter 90, is used to connect the silicone tubing 86 to each segment of PVC tubing 102.

Referring now to FIG. 3B there is shown a side cross-sectional view of the pinch clip 2 in which the clamp 8 is forced into the housing 30. As the clamp 8 moves into the housing 30, the heads 24 of the arms 16 are forced apart by the channels 48, so that the arms are held in a second, open position. This leaves the silicone tube 86 unrestricted by the heads 24, thereby allowing solution to flow freely through the tube.

When the clamp 8 is held in the housing 30, the spring 70 is compressed as is shown in FIG. 3B. However, to maintain the position shown in FIG. 3B, the pinch clip 2 would be placed into a receptacle as shown in FIG. 2, or some other force must be applied to keep the clamp 8 positioned so that the housing 30 is adjacent the flange 14 of the base 12. Thus, if the pinch clip 2 accidently comes out of the receptacle, the spring 70 will force the clamp 8 away from the housing 30 and into the position shown in FIG. 3A. The silicone tube 86 will thereby be occluded, and a free-flow situation cannot develop.

As was discussed regarding FIG. 3A, the adapter 90 nests in the base 12 of the clamp 8 and connects the silicone tube 86 with the PVC tube 102. While this is a convenient place to make the transition between the silicone tube 86 and the PVC tube 102, the change could be made at any other place along the infusion set.

Figure 4:
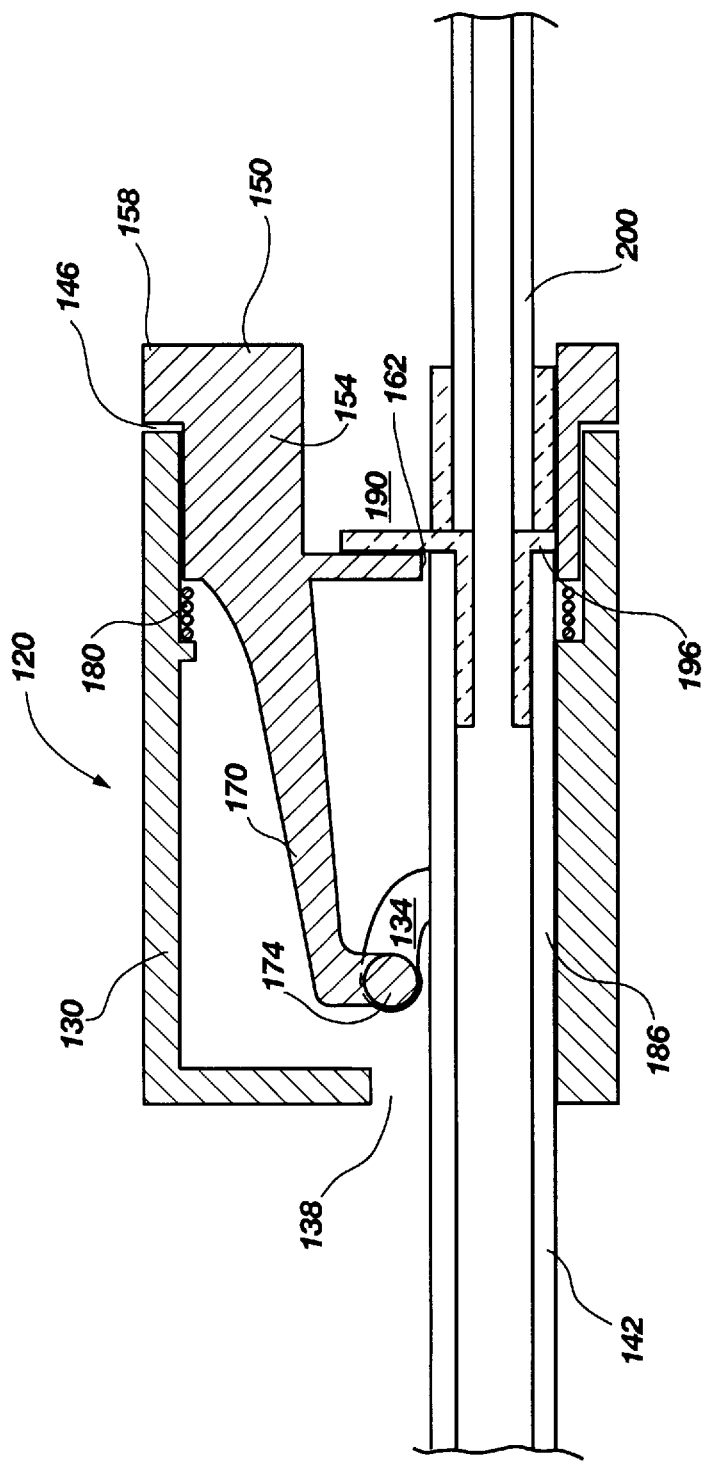
FIG. 4 shows a cross-sectional view of another embodiment of the present invention.

Referring now to FIG. 4, there is shown an alternate embodiment of the present invention. The pinch clip 120 includes a housing 130 with a single channel 134 formed therein. As with the embodiment shown in FIGS. 1–3B, the housing 130 has an open first end 138 for containing a silicone tube 142. The opposing second end 146 is likewise open for receiving the clamp 150. The clamp 150 has a base 154 with a flange 158 and a passage 162 therethrough, similar to the embodiment discussed with respect to FIGS. 1–3B. However, instead of a pair of arms (such as those indicated at 16 in FIGS. 1, 3A and 3B) the embodiment shown in FIG. 4 has a single resilient arm 170 which extends from the base 154. A head 174 of the arm 170 is moveable between a first, closed position in which the head occludes flow through the tube 142 and a second, open position (shown in FIG. 4) in which the head is moved away from the tube so as to allow flow therethrough. A spring 180 is provided to move the base 150 away from the housing 120 and to force the head 174 into the first, closed position.

When force is applied to the clamp 150 so as to move the clamp into the housing 130, the head 174 is pushed away from the tube so as to allow fluid flow therethrough. Thus, the embodiment disclosed in FIG. 4 prevents solution flow through the tube 142 by pinching the tube between the arm 170 and a sidewall 186 the side of the housing 130, as opposed to a pair of arms as discussed above.

As with the previous embodiment, the base 154 of the clamp 150 will typically have a hollow 190 for receiving an adapter 196. The adapter 196 enables the silicone tube 142 to be connected to a PVC tube 200.

Each of the components shown in FIG. 4, with the exception of the spring 180, the silicone tube 142 and the PVC tube 200 will typically be made of a thermo-setting plastic material which is semi-resilient. Such materials are inexpensive and inherently disposable.

Figure 5:
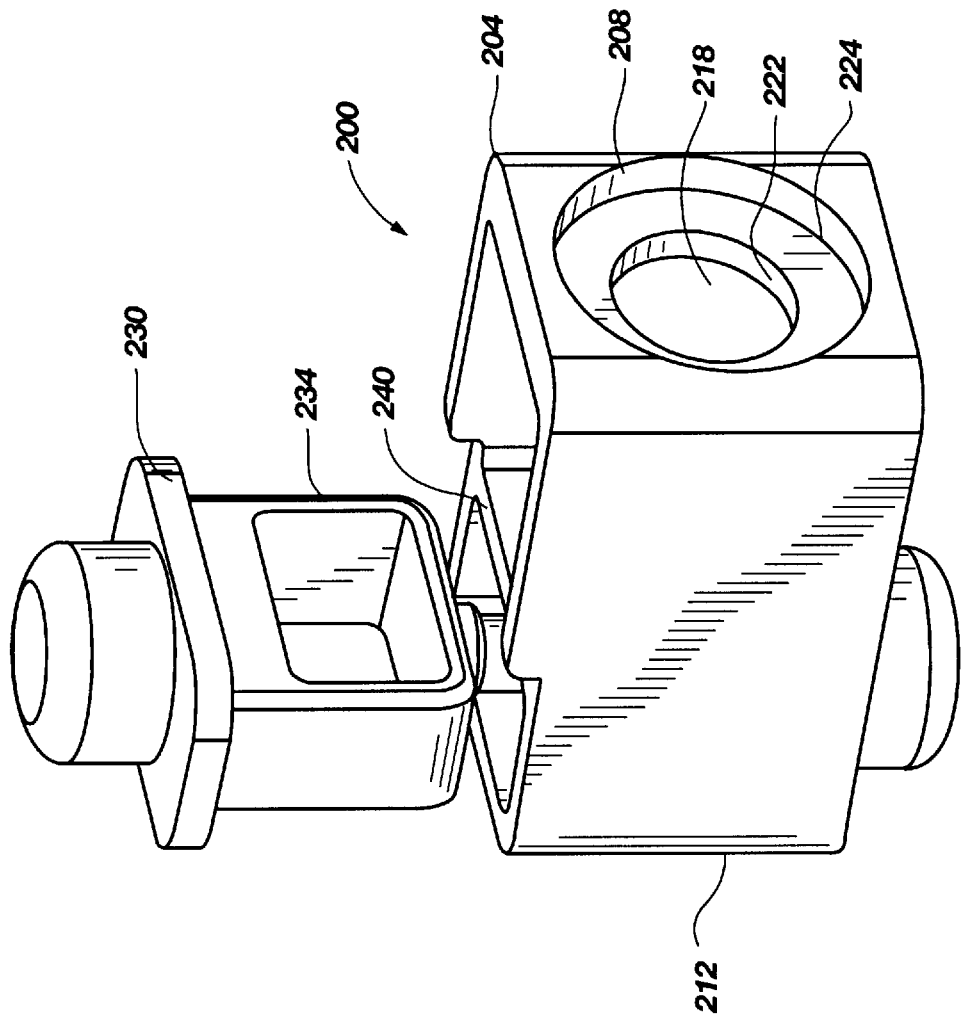
FIG. 5 shows a perspective view of yet another embodiment of the present invention.

Referring now to FIG. 5, there is shown another embodiment of the present invention. The pinch clip occluder, generally indicated at 200, includes a housing 204 having a first end 208 and a second end 212. A passage 218 extends along a long axis of the housing 204 from an opening 222 in the first end 208 to an opening (not shown) in the second end so as to enable the placement of a tube from a delivery set within the passage 218.

The pinch clip occluder 200 further includes a plunger 230 disposed so as to intersect the passage 218. Preferably, a long axis of the plunger 230 will be perpendicular to the long axis of the housing 204 and the passage 218. The plunger 230 includes a plunger passage 234 disposed therein. When the plunger passage 234 and the housing passage 218 are in alignment, fluid flow is allowed through a delivery set (not shown) extending through the housing 204. When the plunger passage 234 and the housing passage 218 are not in alignment, as shown in exaggeration in FIG. 5, flow through the delivery set is prevented as the tubing of the delivery set becomes pinched between the plunger 230 and an inner wall 240 of the housing 204 and a wall defining the opening (not shown) at the second end 212.

Also shown in FIG. 5 is an annular groove 224 which is disposed about the opening in the first end 208 of the housing 204 defining the passage 218. The groove 224 allows an adapter (FIG. 5A) to nest therein so that part of the adapter extends into the housing.

Figure 5A:
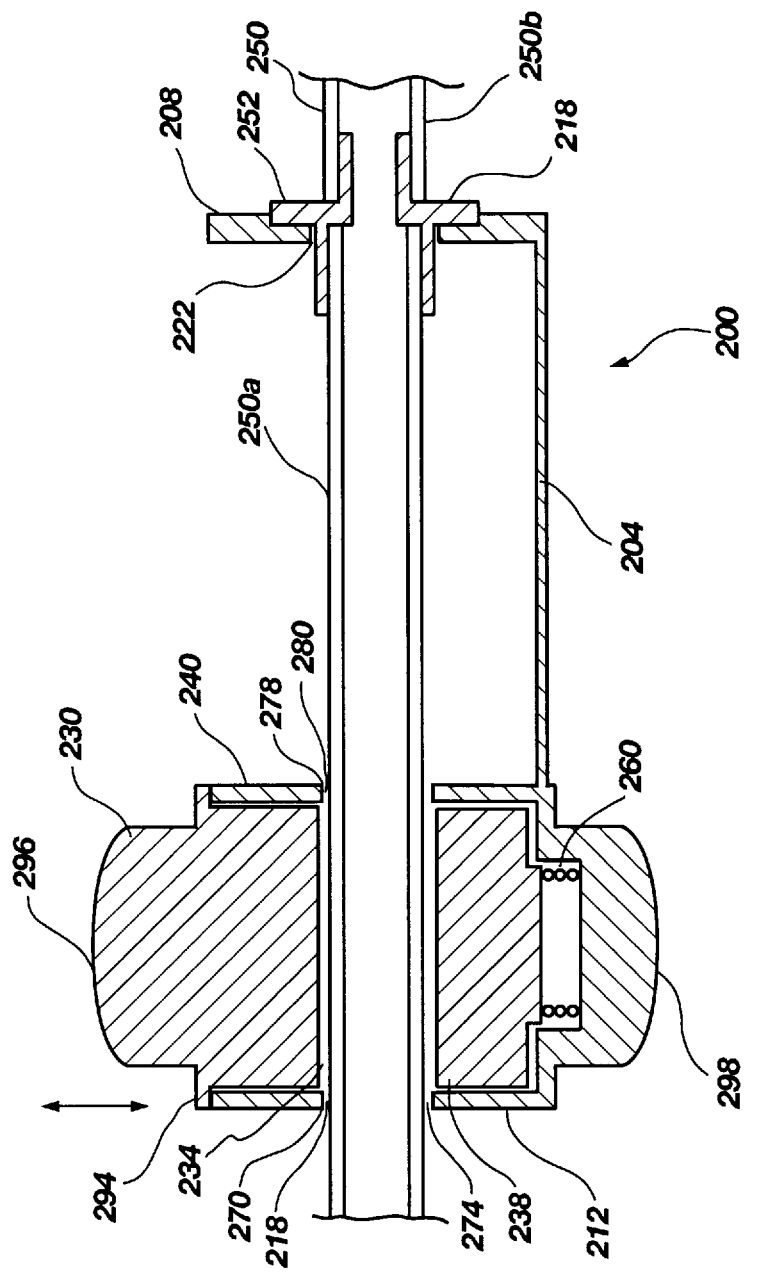
FIG. 5A shows a side cross-sectional view of the embodiment shown in FIG. 5.

Referring now to FIG. 5A, there is shown a cross-sectional view of the pinch clip occluder 200 discussed regarding FIG. 5, as well as a fragmented tube 250 of a delivery set. The tube 250 is positioned in the passage 218 to extend along the passage 218. The plunger 230 is positioned in the housing 204 adjacent the second end 212 so that the plunger passage 234 is in alignment with the housing passage 218. Thus, flow through the tube 250 of the delivery set is not occluded.

As shown in FIG. 5A, the tube 250 has a silicone section 250a and a section 250b made of polyvinylchloride (PVC) or some other suitable material. An adapter 252 nests in the opening 222 and connects the two sections 250a and 250b together. Those familiar with delivery sets for use with enteral feeding pumps and the like will be familiar with such tubes.

For the plunger 230 to be in such a position in normal usage, some external force would need to force the plunger downwardly, as a spring 260 biases the plunger passage 234 into a position not in alignment with the housing passage 218. Thus, when no external pressure is applied to the plunger 230, the spring 260 forces a bottom wall 238 defining the plunger passage 234 upward so as to pinch closed the tube against an upper wall 270 defining an orifice or opening 274 in the second end 212, and an upper wall 278 defining an orifice or opening 280 in the inner wall 240. The tubing 250 through the plunger passage 234 prevents the spring 260 from displacing the plunger 230 out of the housing 204, and an upper stop 294 prevents the plunger passage 234 from passing beyond an alignment position with the housing passage 218. The upper knob 296 disposed above the stop 294 and the lower knob 298 are of similar dimensions so that the housing may be placed in an enteral feeding pump upside down from the position shown in FIGS. 5 and 5A, without affecting functionality.

Figure 6:
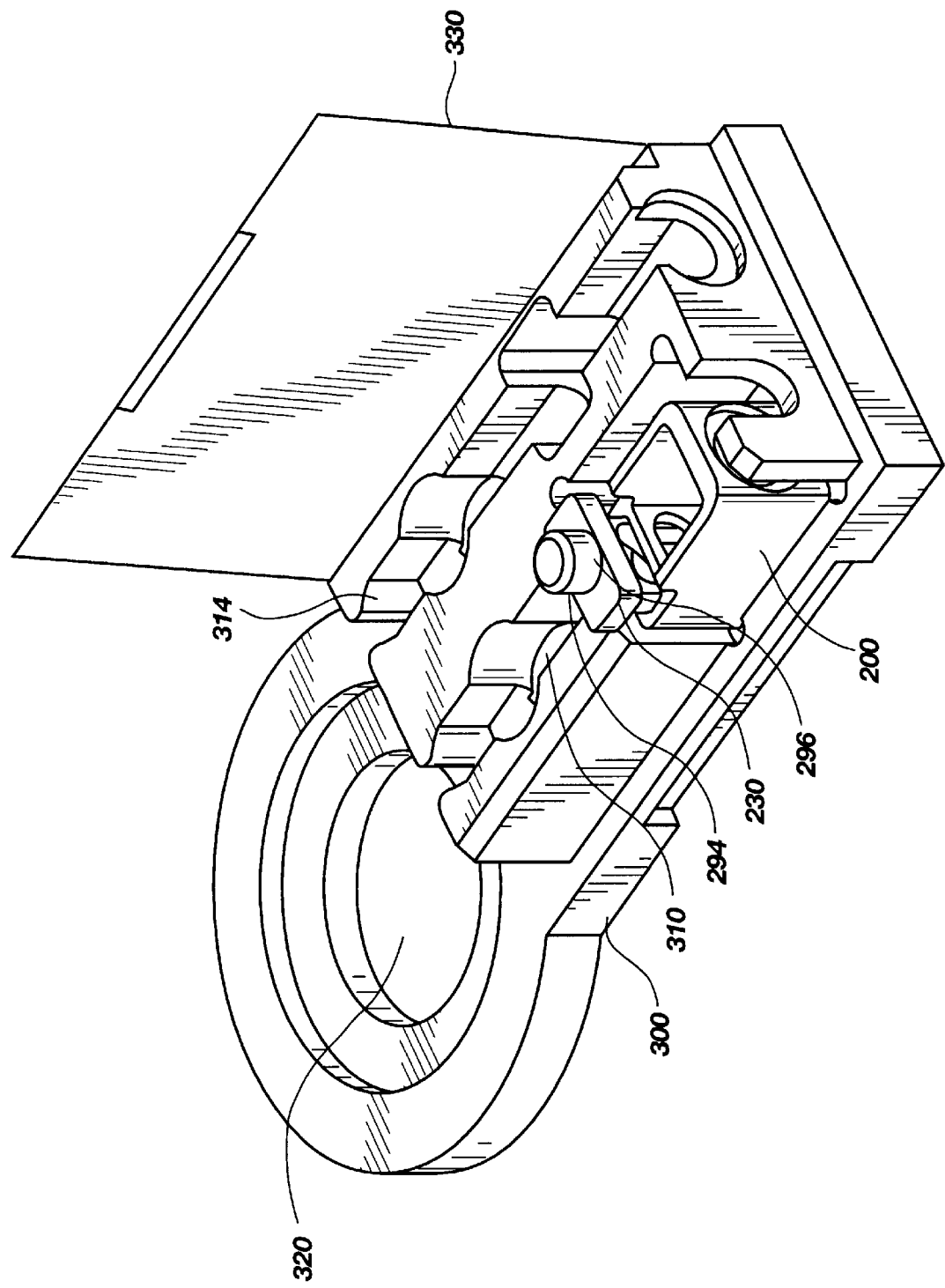
FIG. 6 shows perspective view of the embodiment of the invention discussed regarding FIGS. 5 and 5A positioned in the housing of an enteral feeding pump.

Referring now to FIG. 6, there is shown a pinch clip occluder 200 disposed in the housing 300 for an enteral feeding pump. The enteral feeding pump housing 300 includes a pair of channels 310 and 314 for holding a delivery set tube, such as tube 250 discussed in FIG. 5A. In use, the tube is placed in one channel 310, wrapped about a motor unit (not shown) which is placed in the opening 320, and then positioned in the second channel 314. If the tube is not properly wrapped about the motor unit and placed in the channels 310 and 314 a free-flow condition may develop. However, the present invention prevents such a situation from developing.

As shown in FIG. 6, the pinch clip occluder 200 is positioned along the channel 310. The plunger 230 is positioned so as to occlude flow through a tube disposed in the channel 310. To overcome the biased closed position of the plunger 230, an external force must be applied. This is typically done by closing a cover 330 which is connected to the housing 300. When closed, the cover 330 applies downward force on the plunger 230 so that the plunger passage 234 and the housing passage are in alignment. However, if the tube of the delivery set is not properly loaded in the channels 310 and 314, the cover is unable to close and the plunger 230 is not forced downwardly. Thus, the pinch clip occluder 200 prevents flow through the enteral feeding pump unless the delivery set is properly loaded. Once the cover 330 is closed, the enteral feeding pump may function normally.

In the manner described, a pinch clip occluder for delivery sets is provided. In one embodiment, the pinch clip occluder utilizes a clamping mechanism with at least one arm nested at least partially within a housing which serves as an adjustment mechanism by moving the arm between a position in which the arm occludes flow through and infusion set, and a position in which it allows free-flow through the infusion set. In another embodiment, a moveable plunger which has a plunger passage alignable with a housing passage occludes flow through the housing unless an external pressure is applied.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A pinch clip occluder for selectively preventing flow through two tube sections of an infusion set, the pinch clip occluder comprising:

a housing having an open first end, an open second end and a passage extending from the open first end to the open second end for holding at least one tube section of an infusion set, the housing having a first end wall with an opening formed therein, a second end wall having an opening formed therein, and an inner wall disposed between the first end wall and the second end wall, the inner wall having an opening formed therein, and a contoured knob extending downwardly from the housing for engaging an enteral feeding pump housing so as to secure the pinch clip occluder within the housing when the pinch clip occluder is disposed therein;

plunger means disposed generally transverse to the passage of the housing and positioned between the second end wall and the inner wall for selectively occluding flow through the at least one tube section of an infusion set, the plunger means comprising a plunger passage movable between a first position wherein the plunger passage is not in alignment with the passage through the housing so as to occlude flow through the at least one tube section, and a second position wherein the plunger passage is in alignment with the passage through the housing so as to allow flow through the at least one tube section, and an adapter nestable in the first end for connecting the two tube sections of the infusion set.

2. The pinch clip occluder of claim 1, wherein the adapter is disposed partially within the housing and partially outside of the housing.

3. The pinch clip occluder of claim 1, wherein the adapter is disposed at least partially within the housing.

4. The pinch clip occluder of claim 1, wherein the first end of the housing has an annular groove formed therein for receiving the adapter.

5. The pinch clip occluder of claim 1, wherein the housing is substantially hollow between the first end and the inner wall so as to allow a tube of a delivery set to be slid into the housing from the second end to the first end.

6. The pinch clip occluder of claim 1, wherein the plunger means further comprises a contoured knob for engaging an enteral feeding pump housing so as to secure the pinch clip occluder within the pump housing when the pinch clip occluder is disposed therein.

7. The pinch clip occluder of claim 1, wherein the housing comprises a contoured knob extending downwardly therefrom for engaging an enteral feeding pump housing so as to secure the pinch clip occluder within the housing when the pinch clip occluder is disposed therein.

8. The pinch clip occluder of claim 1 wherein the plunger means further comprises a contoured knob for engaging an enteral feeding pump housing so as to secure the pinch clip occluder within the pump housing when the knob is disposed in contact with the housing, the knobs of the plunger and the housing having substantially the same contour so as to allow the pinch clip occluder with either the knob of the plunger or the knob of the housing pointing down.

9. An occluder for selectively preventing fluid flow through an enteral feeding pump, the occluder comprising:

a housing having an open first end, an open second end and a passage extending from the open first end to the open second end for holding at least one tube section of an infusion set, the housing having a first end wall with an opening formed therein, a second end wall having an opening formed therein, and an inner wall disposed between the first end and the second end, the inner wall having an opening formed therein, each of the openings being of the same size and configured to receive a tube of an enteral feeding pump, and an annular groove being formed in the first end wall about the opening in the first end wall;

plunger means disposed generally transverse to the passage of the housing and positioned between the second end and the inner wall for selectively occluding flow through the at least one tube section of an infusion set, the plunger means comprising a plunger passage movable between a first position wherein the plunger passage is not in alignment with the passage through the housing so as to occlude flow through the at least one tube section, and a second position wherein the plunger passage is in alignment with the passage through the housing so as to allow flow through the at least one tube section, the plunger means having a contoured knob for engaging an enteral feeding pump housing so as to secure the pinch clip occluder within the pump housing when the knob is disposed in contact with the enteral feeding pump housing, and; and a generally continuous infusion tube extending from a position adjacent the first end, through the opening of the inner wall, the plunger passage and through the opening in the second end wall.

10. The occluder of claim 9, wherein the occluder further comprises an adapter for connecting the generally continuous infusion tube to a second infusion tube disposed beyond the first end of the housing.

11. The pinch clip occluder of claim 9, wherein the plunger means further comprises a contoured knob for engaging an enteral feeding pump housing so as to secure the pinch clip occluder within the pump housing when the pinch clip occluder is disposed therein.

12. The pinch clip occluder of claim 9, wherein the housing comprises a contoured knob extending downwardly therefrom for engaging an enteral feeding pump housing so as to secure the pinch clip occluder within the housing when the pinch clip occluder is disposed therein.

13. The pinch clip occluder of claim 9 wherein the housing comprises a contoured knob extending downwardly therefrom for engaging an enteral feeding pump housing so as to secure the pinch clip occluder within the housing when the knob of the housing is disposed in contact with the housing, the knobs of the plunger and the housing having substantially the same contour so as to allow the pinch clip occluder with either the knob of the plunger or the knob of the housing pointing down.

14. An occluder for selectively preventing fluid flow through an enteral feeding pump, the occluder comprising:

a housing having an open first end, an open second end and a passage extending from the open first end to the open second end for holding at least one tube section of an infusion set, the housing having a first end wall with an opening formed therein, a second end having an opening formed therein, and an inner wall disposed between the first end and the second end, the inner wall having an opening formed therein; and plunger means disposed generally transverse to the passage of the housing and positioned between the second end and the inner wall for selectively occluding flow through the at least one tube section of an infusion set, the plunger means comprising a plunger passage movable between a first position wherein the plunger passage is not in alignment with the passage through the housing so as to occlude flow through the at least one tube section, and a second position wherein the plunger passage is in alignment with the passage through the housing so as to allow flow through the at least one tube section; and wherein the plunger means further comprises a contoured knob for engaging an enteral feeding pump housing so as to secure the pinch clip occluder within the pump housing when the knob is disposed in contact with the housing, and the housing comprises a contoured knob extending downwardly therefrom for engaging an enteral feeding pump housing so as to secure the pinch clip occluder within the housing when the knob of the housing is disposed in contact with the housing, the knobs of the plunger and the housing having substantially the same contour so as to allow the pinch clip occluder with either the knob of the plunger or the knob of the housing pointing down.

15. An occluder for selectively preventing fluid flow through an enteral feeding pump, the occluder comprising:

a housing having an open first end, an open second end and a passage extending from the open first end to the open second end for holding at least one tube section of an infusion set, the housing having a first end wall with an opening formed therein, a second end having an opening formed therein, and an inner wall disposed between the first end and the second end wall, the inner wall having an opening formed therein, the housing comprising a contoured knob extending downwardly therefrom configured for engaging an enteral feeding pump housing so as to secure the pinch clip occluder within the housing when the pinch clip occluder is disposed therein; and plunger means disposed generally transverse to the passage of the housing and positioned between the second end and the inner wall for selectively occluding flow through the at least one tube section of an infusion set, the plunger means comprising a plunger passage movable between a first position wherein the plunger passage is not in alignment with the passage through the housing so as to occlude flow through the at least one tube section, and a second position wherein the plunger passage is in alignment with the passage through the housing so as to allow flow through the at least one tube section.

* * * * *